United States Patent [19]

Johnson et al.

[11] Patent Number: 4,531,518

[45] Date of Patent: Jul. 30, 1985

[54] METHOD FOR INHIBITING THE DEVELOPEMENT OF BREAST BLISTERS ON POULTRY

[75] Inventors: Gary M. Johnson, Wallace, N.C.; Glen L. Heuberger, Clarendon Hill, Ill.

[73] Assignee: Swift & Company, Oak Brook, Ill.

[21] Appl. No.: 531,066

[22] Filed: Sep. 12, 1983

[51] Int. Cl.³ .................. A61B 17/36; A01K 29/00
[52] U.S. Cl. .................. 128/303.1; 119/143; 128/92 R
[58] Field of Search .......... 128/303.1, 92 R, 92 G; 119/143, 159, 160

[56] References Cited

U.S. PATENT DOCUMENTS

| | | | |
|---|---|---|---|
| 1,230,843 | 6/1917 | Bird | 119/159 |
| 1,508,749 | 9/1924 | Kuehn | 119/159 |
| 3,083,688 | 4/1963 | Tillotson | 119/143 |
| 3,101,696 | 8/1963 | Lipman | 119/143 |
| 3,143,099 | 8/1964 | Poole et al. | 119/143 |
| 3,192,903 | 7/1965 | Vandepopuliere | 119/143 |
| 3,403,683 | 10/1968 | Koonz et al. | 128/303.14 |
| 4,116,199 | 9/1978 | Bryne | 128/303.1 |
| 4,292,973 | 10/1981 | Yamauchi et al. | 128/303.1 |
| 4,376,376 | 3/1983 | Gregory | 128/303.1 |

OTHER PUBLICATIONS

Bojrab, M. J., Veterinary Cryosurgery–An Overview, Norden News, pp. 16–19–Spring 1978.
Joyce, Joseph R., Cryosurgical Treatment of Tumors of Horses and Cattle, J. AVMA 168(3) 226–229, (1976).

*Primary Examiner*—Gene Mancene
*Assistant Examiner*—C. W. Shedd
*Attorney, Agent, or Firm*—Edward T. McCabe

[57] ABSTRACT

Live poultry, soon after hatching, are treated with a cryogenic fluid applied at the keel bone tip for a brief period sufficient to retard growth of the keel bone tip but insufficient to damage skin or tissue and thereby reduce breast blister and other dermal growths and increase the market quality of birds at maturity.

7 Claims, No Drawings

METHOD FOR INHIBITING THE DEVELOPEMENT OF BREAST BLISTERS ON POULTRY

This invention relates to a method of inhibiting skin blister in poultry and more particularly to an improved method for preventing breast blisters.

Breast blisters are an unsightly defect in poultry which result in the down grading of birds with a consequent loss in value. These blisters consist of swellings of the tissue adjacent to the ventral edge of the keel bone (sternal crest). They may vary in size from a few millimeters to more than two inches in length. They may be colorless and filled with a clear exudate, or they may be red to blue in color and have a bloody exudate.

When a breast blister is large or discolored enough to render the dressed poultry unsightly in appearance it must be removed by cutting. The carcasses with cut skin will then be put in B or C grade class resulting in a monetary loss of several cents per pound depending upon the price schedule for the dressed poultry classes. Breast blisters are more prominent and prevalent on male birds than on female birds, and become more severe as the birds get older and heavier. Chickens and turkeys are both prone to breast blisters. Birds which are raised in cages or batteries have a higher incidence of breast blisters than birds raised in floor pens or on the range. The origin of these blisters has been ascribed to a variety of causes, including bacterial and viral infections, and irritation of the skin and subcutaneous tissues or pressure against the keel bone. Prevalence of the problem is also affected by season of the year and certain geographical areas are known to have a higher incidence of breast blisters in poultry.

Various feeding and management procedures have been tried to eliminate or prevent the blisters. None have proved to be completely successful. Protective shields of solidified cohesive material covering the keel bone area of fowl have been proposed. Examples are shown in U.S. Pat. No. 3,083,688 to Tillotson and No. 3,143,099 to Poole, et al. Difficulty has been encountered in providing a shield which will accommodate the rapid growth of young poultry and also is economically affixing the shield to the fowl in a manner so that the fowl remains protected during the relatively long period of time that poultry are vulnerable to breast blisters.

Another means of effective inhibition of breast blisters herefore known has been the surgical removal of the tip of the keel bone when the bird is about 1 to 3 days old, as disclosed in U.S. Pat. No. 3,403,683 to Koonz, et al. That procedure is, however, difficult to perform on small birds, risks infection and may cause deformities.

Accordingly, it is an object of this invention to provide a rapid economical and improved method of inhibiting breast blister in poultry.

Another object of the invention is to provide an improved method of preventing breast blister in poultry by retarding growth of the anterior tip of the keel bone of young poultry.

A further object of the invention is to provide an improved method for preventing breast blister in poultry by application of cryogenic cold fluid to the skin covering the anterior tip of the keel of the poultry which results in the bone tip developing a rounded shape.

The basic procedure of the present invention is to produce a rounded keel bone tip in poultry, particularly turkeys, by treating the keel bone tip of chicks and poults, and the like, at a very young age, with a cryogenically cold fluid applied topically at the skin over the bone tip for a duration sufficient to retard future bone growth in that area yet not to cause any substantial incidents of lesions or other damage to the poultry skin and flesh.

Further objects and advantages of the present invention will become apparent to the reader of the following detailed specification.

Young birds within about one week of hatch, and preferably of 1 to 3 days age, are treated individually by a skilled operator who first grasps the bird in a first hand placed across the back of the bird so as to leave the breast area exposed. The bird is held with its head pointing slightly downward and away from the operator. Preferably, the operator using the end of his index finger, of the first hand, accurately locates the keel bone tip and momentarily covers the bone tip with that finger. Then with the other, second hand, the operator aims a closely confined spray of cryogenic fluid at the breast area over the keel bone tip and at the same time removes the index finger from that area. The cryogenic fluid spray is then applied to only the breast area directly covering the keel bone tip for a brief treatment period insufficient to damage the skin but sufficient to cause retardation of bone growth.

Preferably, the area of spray contact is confined by utilizing a cone extending from a spray source, such as a nozzle or orifice, to the target breast area. In this way the contact area on the bird may be accurately localized and controlled and the entire quantity of cryogenic fluid applied thereto. In positioning the spray cone, the operator should allow for leakage to be directed outwardly toward the crop area of the bird and not toward breast tissue.

It has been found that the treatment period (cryogenic spray application) usually is about 2.5 to 10 seconds depending on the temperature of the cryogenic fluid and the effective skin contact area of the spray pattern, the latter being circular areas of about 5 millimeters to 10 millimeters in diameter. When using liquid nitrogen it was found that the incidence of skin lesions and other defects was very low when the treatment period was 2.5–6 seconds; and the preferred practice is to apply liquid nitrogen through a 5 mm cone for a period of 2.5 seconds.

Liquid nitrogen is believed to produce operative temperatures of as low as $-196°$ C. However, it is not believed that such a low temperature is actually imparted or achieved in the poultry skin or underlying tissue and bone. However, compared to other available cryogens, liquid nitrogen is believed to be the coldest and will produce the most rapid freeze and has the deepest and fastest penetration characteristics. Examples of other cryogens that may be effective at relatively longer treatment periods are nitrous oxide (about $-80°$ C.) and carbon dioxide (about $-78°$ C.). Liquified air and oxygen may also be useful.

The foregoing cryogens and the specific apparatus for emanating a controlled cryogenic fluid spray as well-known in the art of cryosurgery, including surgical treatment of animals. (See Joyce "Cryosurgical Treatment of Tumors of Horses and Cattle", *Journal of the American Veterinary Medical Association*, 1976, Vol. 168, No. 3; and Goldstein and Hess "Cryosurgery of Canine and Feline Tumors", *The Journal of the American Animal Hospital Association,* May/June 1976, Vol 12.) However, an important distinction between the prresent invention and cryosurgery is that the latter is understood to involve the freezing of tissue to the extent that the operative target is destroyed and the target, such as a tumor, along with surrounding tissue and overlying skin, which is also destroyed, gradually sloughs off and leaves a scar. On the other hand, the present invention properly applied does not appear to result in any discernible skin or tissue destruction or scarring. Indeed, by properly confirming the cryogenic spray and applying same for minimal time periods, such damage may be completely avoided; and even where somewhat greater application of cryogen is involved the resultant defect, if any, may not be any worse than misshaped keel bone or assymetrical breast conformation in the matured bird. Thus, the present technique is devised to avoid the manner of cryosurgical procedures.

The apparatus employed in carrying out the invention and in the following examples is a modified form of equipment commercially available for cryosurgical use. Two types of equipment were used in the examples, both distributed by Frigitronics, Inc. of 770 River Road, Shelton, Conn. 06484, and both employ liquid nitrogen as the cryogenic fluid. Among the following examples the first four (I through IV) utilized Frigitronics "CS-76 Cryosurgical Unit" and the latter examples (V through VII) employed the "CE-8 Cryosurgical System". Both types of equipment include a refrigerant control assembly, a probe handle, and an flexible insulated delivery line connecting the control assembly to the probe handle. The probe handle terminates in a tip that may be cooled for conductive contact with tissue or, alternately, a spray tip that emits a spray of gas and liquid. The present invention utilizes the spray tip. Additionally, the equipment control assembly includes a flow control valve to regulate rate of nitrogen flow between full open and closed limits. While the valve is set to an open position the nitrogen will flow to the probe handle although the rate of flow may vary with changes in pressure and in temperature of the delivery line during operation. Changes in the flow rate will alter the pattern of spray emitted from the probe spray tip; and we have provided for uniformity of pattern by projecting the spray through small cones of approximately 20 millimeters length with an open circular end of 5 and 10 millimeters in diameter attached to the probe handle over the spray tip. The two types of equipment differ in that the "CS-76" unit is portable and includes a small self-contained supply of nitrogen which the control assembly releases in pulses that may be adjusted for time duration. The "CE 8" equipment is mountable on an insulated 30 liter supply container and liquid nitrogen is delivered continuously when the valve is opened.

The following examples represent the evolution of the present invention and demonstrate the working parameters for one cryogenic fluid, namely, liquid nitrogen.

EXAMPLE I

In an initial test to determine if cryogenic treatment could retard the breast bone without tissue damage 125 "cull" tom (male) poults of Nicholas breed were divided into five groups of 25 poults each and treated with liquid nitrogen spray according to the following schedule but without placing the spray cone into contact with the poultry skin:

| Group | Spray Cone Diameter | Duration of Spray |
|-------|---------------------|-------------------|
| A | 10 mm | 3 sec. |
| B | " | 4 sec. |
| C | " | 5 sec. |
| D | " | 6 sec. |
| E | 5 mm | 5 sec. |

Three days later all birds were inspected visually and no change in bone conformation was found. The birds were then regrouped and retreated at one week of age according to the following schedule and with the end of the spray cone held against the poultry skin:

| Group | Spray Cone Diameter | Duration |
|-------|---------------------|----------|
| F | Control - no treatment | |
| G | 10 mm | 5 sec. |
| H | " | 10 sec. |
| I | " | 15 sec. |
| J | " | 20 sec. |

After two additional weeks the poults were dispatched and examined with the following results: Group F and G poults displayed no damage or change to the dermal layers or keel bone. Group H, I and J poults lacked the protruding tip of the keel bone but showed visible white scale at the treatment site; and in Groups I and J a large percentage of the poults had cyst-like sores at the treatment site. Accordingly, the 10-second treatment appeared the better of this test although it did produce visible skin tissue damage.

EXAMPLE II

A group of 453 Nicholas breen tom (male) turkey poults were treated on the day hatched by a 10 second application of cryogenic nitrogen to a confined area of skin 10 mm diameter over the keel bone tip to determine if breast blisters would thereby be reduced. A second larger group of 1861 poults of the same age was not treated but raised separately under substantially the same conditions (except different quantities of feed were provided); and both groups were dispatched, processed and examined at 18 weeks of age with the following results (both groups experienced a relatively normal mortality loss of approximately 8%):

453 cryogenic treated
414 survived and examined
5 breast blisters (1.3%)
8 breast buttons (1.98%)
1861 untreated
1707 survived
146 breast blisters (8.29%)
98 breast buttons (5.56%)

In addition to the markedly reduced incidence of breast blisters, the treated group at dispatch showed a significant incidence of breast conformation deformities—usually a large depression at one side of the breast—believed to have resulted from muscle tissue cell destruction caused by too great an exposure to the liquid nitrogen. The deformities caused a disproportionate downgrading in the treated group which produced only 35.2% top grade carcasses as compared to 56.8% top grade from the untreated group. Thus, breast blisters had been inhibited but the treatment conditions were less than optimum from the standpoint of tissue damage and quality grade loss.

EXAMPLE III

A further series of tests to refine treatment conditions was performed on 100 Hybrid 2,000 breed tom (male) poults divided evenly into four groups and utilizing a 5 mm diameter open end spray cone. The poults of the respective groups were treated with confined sprays of cryogenic nitrogen of 4, 6, 8 and 10 second duration. Most of the birds were dispatched and examined at 16 weeks age with the following results:

| Group | Number Examined | Spray Duration | Breast Defects | Unaffected Keel Tip |
|---|---|---|---|---|
| A | 24 | 4 | 1 | 7 |
| B | 21 | 6 | 1 | 0 |
| C | 21 | 8 | 3 | 0 |
| D | 18 | 10 | 3 | 0 |

The birds of Group B demonstrated the best overall breast conformation.

EXAMPLE IV

A large number of Nicholas breed tom turkey poults were divided into a control group of several thousand poults which was given no treatment, and a test group of 750 poults each treated by applying a 6 second cryogenic spray of nitrogen through a cone having an open end 5 mm in diameter placed against the skin over the keel bone tip of each poult. This test was conducted from mid-July (birth) to dispatch of the birds in mid-November and there was no evidence of breast blisters among the control group and a low incidence of breast buttons. Examination of the birds when dispatched and processed showed the same percentage of both groups received top quality grade (84.7% of those treated and 84.6% of the control). The treated birds were on average 5% lower weight, however the treated group experienced only 14.1% mortality whereas the combined groups showed 19% mortality, mostly caused by rotovirus infection at about 4–6 weeks age.

EXAMPLES V, VI, VII and VIII

In each of these four tests several thousand tom poults comprising one-half of a flock were treated with liquid nitrogen applied through the above-described "CE 8" equipment. Liquid nitrogen flow was essentially continuous and exposure time for each poult was controlled by the operator adapting a uniform rhythmic count between implacing and removing the open end of a 5 mm diameter spray cone on each poult. The four tests were conducted sequentially from hatch dates in late February through early April at three southern farm locations. Test V birds were range grown on one farm, tests VI and VII birds were raised in confinement at a second farm, and test VIII birds were raised in confinement on a third farm. Observations of skin lesions on approximately 75% of the poults treated in the first two tests (Examples V and VI) led to reductions in treatment time and to the step of initially locating the keel bone tip with an index finger. It was also found that 400–500 poults per hour could be treated by a single operator, and approximately 3200–4000 poults could be treated with 30 liters of liquid nitrogen.

| Example (Test) | Number of Poults | Approximate Duration of $N_2$ Treatment |
|---|---|---|
| V | 3251 | 3.5 sec. |
| VI | 6000 | 3.5 sec. |
| VII | 5500 | 3.0 sec. |
| VIII | 5000 | 2.5 sec. |

Although skin lesions developed on approximately 75% of the poults in tests V and VI they were generally small (about 1 mm thick, 2 mm wide and 1–2 mm long) and did not involve tissue lesions or abnormalities. Very few poults of test VII and none of test VIII developed any observable lesions. The following table summarizes the results of these four tests:

| Example (Test) | Poults Placed | Liquid N2 Treatment (sec.) | Market Age Wk./days | Avg. Wt. (lbs.) | Top Grade (%) | Breast Buttons (%) | Breast Blisters (%) | Breast Defects (%) | Condemnation (%) | Mortality (%) |
|---|---|---|---|---|---|---|---|---|---|---|
| V | control 3,249 | 0 | 17/6 | 20.74 | 75.9 | 16.61 | — | — | — | — |
|  | cryogenic 3,251 | 3.5 | 17/6 | 20.44 | 30.3 | 1.89 | — | 22.01 | 2.64 avg. | 9.6 avg. |
| VI | control 6,000 | 0 | 17/4 | 20.3 | 80.4 | 3.90 | — | — | — | 6.95 |
|  | cryogenic 6,000 | 3.5 | 17/3 | 19.65 | 66.6 | 0.90 | — | 20.92 | 2.53 avg. | 7.57 |
| VII | control 6,000 | 0 | 18/3 | 21.18 | 81.9 | 2.54 | — | — | 3.29 | 8.0 avg. |
|  | cryogenic 5,500 | 3.0 | 18/2 | 21.23 | 76.6 | 1.57 | — | 5.28 | 4.20 | — |
| VIII | control 5,000 | 0 | 19/0 | 20.02 | 63.63 | — | 6.5 | — | 3.35 | 8.27 avg. |
|  | cryogenic 5,000 | 2.5 | 19/0 | 19.64 | 67.54 | — | 7.0 | — | 4.75 | — |

Data from these tests is irregular concerning breast blisters, however there is a definite showing that similar dermal growths (buttons) are reduced by cryogenic treatment and defects caused by the treatment may be substantially eliminated by control of treatment duration.

Obviously, many modifications and variations of the invention as heretofore set forth may be made without departing from the spirit and scope thereof, and therefore only such limitations should be imposed as are indicated in the appended claims:

We claim:

1. An approved method for inhibiting the development of breast blisters on poultry comprising: applying to a confined area of skin covering the anterior tip of the keel bone of young live poultry, a spray of a cryogenic cold fluid for a brief period sufficient to retard future growth of the keel bone tip, said period being insufficient for the cryogenic cold fluid to cause significant visible damage to said skin and underlying tissue.

2. The method of claim 1 wherein the cryogenic cold fluid is nitrogen.

3. The method of claim 1 wherein the confined area of skin is about 5–10 mm in diameter.

4. The method of claim 3 wherein the cryogenic cold fluid is nitrogen.

5. The method of claim 4 wherein said brief period is within the range of about 2.5–10 sec.

6. The method of claim 4 wherein said brief period is within the range of about 2.5–6 sec.

7. The method of claim 1 wherein an operator first grasps a poultry with one hand placed across the poultry back side and locates and covers the anterior tip of the poultry keel bone with the index finger of that hand, and the operator then implaces the said spray of cryogenic cold fluid with his other hand immediately after removing his index finger from the keel bone tip and while continuing to hold the poultry.

* * * * *